(12) United States Patent
Kurihara et al.

(10) Patent No.: US 7,888,615 B2
(45) Date of Patent: Feb. 15, 2011

(54) FLAT DETECTOR AND MEDIUM DETECTOR

(75) Inventors: Eizo Kurihara, Kanagawa (JP);
Tsukasa Matsuda, Kanagawa (JP);
Kunihiro Takahashi, Kanagawa (JP);
Hiroyoshi Inoue, Kanagawa (JP); Mario Fuse, Kanagawa (JP); Shoji Yamaguchi, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 0 days.

(21) Appl. No.: 12/434,163

(22) Filed: May 1, 2009

(65) Prior Publication Data

US 2010/0116722 A1 May 13, 2010

(30) Foreign Application Priority Data

Nov. 12, 2008 (JP) ............................ 2008-289642

(51) Int. Cl.
*B07C 5/344* (2006.01)
(52) U.S. Cl. ....................... 209/576; 324/234
(58) Field of Classification Search ................. 209/534, 209/552, 567, 569, 926; 324/234
See application file for complete search history.

(56) References Cited

U.S. PATENT DOCUMENTS

| | | | |
|---|---|---|---|
| 2,276,011 A | | 3/1942 | Billstein |
| 2,550,736 A | * | 5/1951 | Tricebock .................... 324/243 |
| 2,810,880 A | * | 10/1957 | Buccicone .................. 324/243 |
| 3,618,765 A | * | 11/1971 | Cooper et al. ............... 209/534 |
| 3,996,510 A | * | 12/1976 | Guichard .................... 327/510 |
| 4,326,636 A | * | 4/1982 | Kawakami ................... 209/534 |
| 5,402,895 A | * | 4/1995 | Mikkelsen et al. ........... 209/534 |
| 5,801,530 A | * | 9/1998 | Crosby et al. .............. 324/207.26 |
| 5,814,986 A | * | 9/1998 | Goskowicz et al. .......... 324/207.26 |

(Continued)

FOREIGN PATENT DOCUMENTS

JP   A-2007-74334   3/2007

(Continued)

OTHER PUBLICATIONS

Stupakov et al., "Governing conditions of repeatable Barkhausen noise response," *Journal of Magnetism and Magnetic Materials*, Sep. 1, 2009, pp. 2956-2962, vol. 321, No. 18, Elsevier Science Publishers, Amsterdam, NL.

(Continued)

*Primary Examiner*—Joseph C Rodriguez
(74) *Attorney, Agent, or Firm*—Oliff & Berridge, PLC (57) ABSTRACT

A flat detector includes a first flat member and a second flat member both made of a nonmagnetic nonmetal, a first conductive wiring that generates an alternating magnetic field, the first conductive wiring being disposed on a surface of the first flat member facing toward the second flat member, a first layer made of a nonmagnetic metal and disposed at least on a surface of the first flat member, a second conductive wiring that detects a signal generated by magnetization reversal of a magnetic material, the magnetization reversal being caused by the alternating magnetic field generated by the first conductive wiring, the second conductive wiring being disposed on a surface of the second flat member facing toward the first flat member, and a second layer made of a nonmagnetic metal and disposed at least on a surface of the second flat member.

8 Claims, 5 Drawing Sheets

U.S. PATENT DOCUMENTS

| | | | |
|---|---|---|---|
| 6,636,037 B1 | 10/2003 | Ou-Yang | |
| 7,102,347 B2 * | 9/2006 | Kondo | 324/239 |
| 2006/0076945 A1 * | 4/2006 | Takahashi et al. | 324/76.11 |
| 2009/0189600 A1 * | 7/2009 | Kurkovskiy | 324/207.16 |

FOREIGN PATENT DOCUMENTS

| | | |
|---|---|---|
| JP | A-2007-88812 | 4/2007 |
| JP | A-2007-323431 | 12/2007 |
| JP | A-2008-070948 | 3/2008 |
| JP | A-2008-85779 | 4/2008 |

OTHER PUBLICATIONS

Mar. 10, 2010 Search Report issued in European Patent Application No. EP 09 16 2966.

May 21, 2010 Office Action issued in Australian Patent Application No. 2009202422.

* cited by examiner

FIG. 9

FLAT DETECTOR AND MEDIUM DETECTOR

CROSS-REFERENCE TO RELATED APPLICATION

This application is based on and claims priority under 35 USC 119 from Japanese Patent Application No. 2008-289642 filed Nov. 12, 2008.

BACKGROUND

1. Technical Field

The present invention relates to a flat detector and a medium detector.

2. Related Art

With a flat detector in which the magnetization of a magnetic material is reversed by the use of an alternate field so as to detect a signal that is generated by the magnetization reversal so generated, there is a problem that exterior noise is erroneously detected.

SUMMARY

An object of the invention is to suppress the erroneous detection of exterior noise by such a flat detector.

According to an aspect of the invention, a flat detector includes a first flat member and a second flat member both made of a nonmagnetic nonmetal, the first flat member and the second flat member being disposed to face each other with a space therebetween for transporting a sheet-like medium, a first conductive wiring that generates an alternating magnetic field, the first conductive wiring being disposed on a surface of the first flat member facing toward the second flat member, a first layer made of a nonmagnetic metal and disposed at least on a surface of the first flat member opposite to the surface on which the first conductive wiring is disposed, a second conductive wiring that detects a signal generated by magnetization reversal of a magnetic material contained in the sheet-like medium, the magnetization reversal being caused by the alternating magnetic field generated by the first conductive wiring, the second conductive wiring being disposed on a surface of the second flat member facing toward the first flat member and a second layer made of a nonmagnetic metal and disposed at least on a surface of the second flat member opposite to the surface on which the second conductive wiring is disposed.

According to the aspect of the invention, compared with a case where the configuration described in the aspect is not provided, it becomes possible to suppress better the erroneous detection of exterior noise.

BRIEF DESCRIPTION OF THE DRAWINGS

Exemplary embodiments of the invention will be described in detail based on the following figures, wherein.

DETAILED DESCRIPTION

Hereinafter, a best mode for carrying out the invention (hereinafter, referred to as exemplary embodiments) will be described. Note that the description will be made in the following order.

1. Configuration of Flat Panel Detector (first to sixth exemplary embodiments and other exemplary embodiments)

2. Medium Detector (Detector Configuration, Medium Detecting Operation, Applied Examples)

<1 Configuration of Flat Panel Detector>

First Exemplary Embodiment

Figure 1:
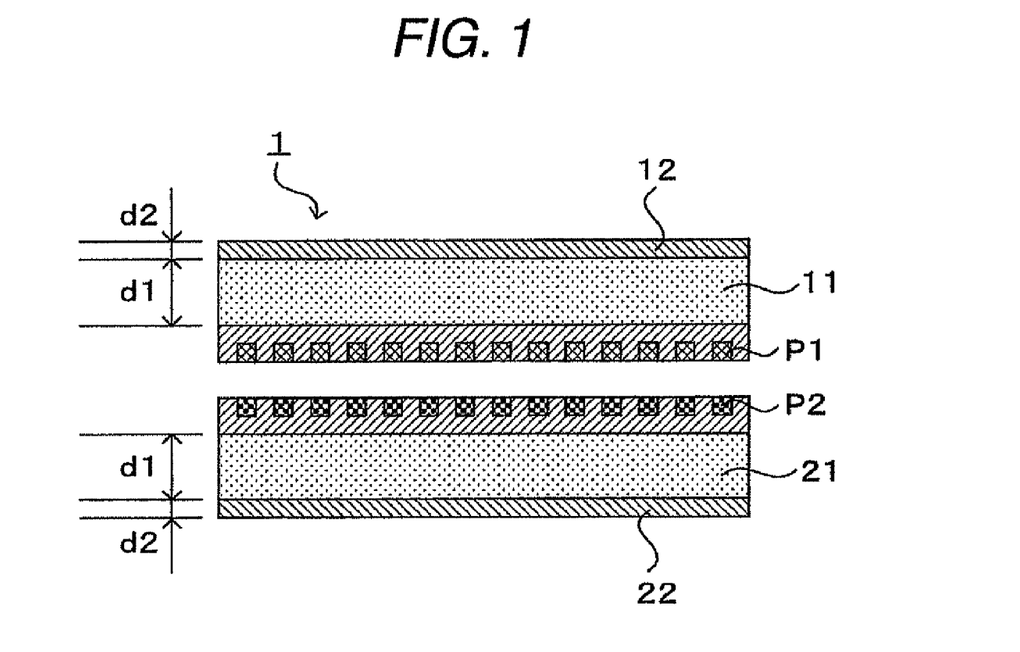
FIG. 1 is an exemplary sectional view illustrating the configuration of a flat detector according to a first exemplary embodiment.

FIG. 1 is an exemplary sectional view illustrating the configuration of a flat detector according to a first exemplary embodiment. This flat detector 1 has a first conductor wiring P1 which generates an alternate field, a first holding material 11 which holds the first conductor wiring on one side thereof, a first laminated material 12 (first layer) which is provided on the other side of the first holding material 11, a second conductor wiring P2 which detects a signal which is generated by a magnetic material which configures an object to be detected being reversed in magnetization upon receipt of the alternate field generated from the first conductor wiring P1, a second holding material 21 which holds the second conductor wiring P2 on one side thereof, and a second laminated material 22 (second layer) which is provided on the other side of the second holding material 21.

The first conductor wiring P1 is such as to be used as a transmission antenna of the flat detector, and a wiring construction thereof is such that for example, the block pattern (conductor) is formed on an insulation material. A substantially uniform alternate field is generated by a current flowing through the first conductor wiring P1. When a magnetic material which configures an object to be detected passes by in the vicinity of the first conductor wiring P1, the magnetization of the magnetic material is reversed by the alternate current generated from the first conductor wiring P1.

The first holding material 11 is a base material which holds the first conductor wiring P1 by allowing the first conductor wiring P1 to be attached to the one side thereof. The one side of the first holding material 11 also functions to specify a surface configuration of the first conductor wiring P1. For example, in the event that the first conductor wiring P1 is planar, the one side of the first holding material 11 becomes planar to match the plane of the first conductor wiring P1. Alternatively, in the event that the first conductor wiring P1 has a curved surface, to match the curved surface of the first conductor wiring P1, the one side of the first holding material 11 is formed into a curved surface. The first holding material 11 is made of a nonmagnetic nonmetal, and compared with a case where it is made of a metal, the generation of eddy current is suppressed better. For example, resin, glass or wood is used.

A thickness d1 of the first holding material 11 is made to be a thickness which is equal to or larger than such a distance that the magnetic field strength of an alternate field generated by the first conductor wiring P1 becomes one gauss or smaller. By the thickness of the first holding material 11 being set to the thickness d1, eddy current, which will be described later, flowing through the first laminated material is suppressed. In addition, an upper limit of the thickness d1 is practically such that the magnetic field strength of an alternate field to be generated becomes of the order of 0.05 gauss.

The first laminated material 12 is attached to the other side of the first holding material 11. The first laminated material 12 is made of a nonmagnetic metal. For example, aluminum, copper, stainless steel, brass, titanium, or zinc is used. Exterior noise is blocked out by this first laminated material 12.

A thickness d2 of the first laminated material 12 is 10 μm or larger and 1 mm or smaller. In case the thickness d2 is 10 μm or larger, exterior noise can be blocked out so as to suppress effects on the alternate field generated by the first conductor wiring P1. An upper limit of the thickness d2 of the first laminated material 12 is practically desired to be 1 mm or smaller.

The second conductor wiring P2 is such as to be used as a reception antenna of the flat detector 1 and a wiring construction thereof is such that for example, the block pattern (conductor) disclosed in Patent Document 3 is formed on an insulation material. The second conductor wiring P2 detects as a current value a signal (large Barkhausen signal) which is generated by the magnetic material which configures the object to be detected being reversed in magnetization upon receipt of the alternate field generated from the first conductor wiring P1.

The second holding material 21 is a base material which holds the second conductor wiring P2 by allowing the second conductor wiring P2 to be attached to the one side thereof. The one side of the second holding material 21 also functions to specify a surface configuration of the second conductor wiring P2. For example, in the event that the second conductor wiring P2 is planar, the one side of the second holding material 21 becomes planar to match the plane of the second conductor wiring P2. Alternatively, in the event that the second conductor wiring P2 has a curved surface, to match the curved surface of the second conductor wiring P2, the one side of the second holding material 21 is formed into a curved surface. The second holding material 21 is made of a nonmagnetic nonmetal, for example, resin, glass or wood is used.

A thickness d1 of the second holding material 21 is made to be a thickness which is equal to or larger than such a distance that the magnetic field strength of an alternate field generated by the second conductor wiring P2 becomes one gauss or smaller. By the thickness of the second holding material 21 being set to the thickness d1, eddy current, which will be described later, flowing through the second laminated material 22 is suppressed. In addition, an upper limit of the thickness d1 is practically such that the magnetic field strength of an alternate field to be generated becomes of the order of 0.05 gauss.

The second laminated material 22 is attached to the other side of the second holding material 21. The second laminated material 22 is made of a nonmagnetic metal. For example, aluminum, copper, stainless steel, brass, titanium, or zinc is used. Exterior noise is blocked out by this second laminated material 22.

A thickness d2 of the second laminated material 22 is 10 μm or larger and 1 mm or smaller. In case the thickness d2 is 10 μm or larger, exterior noise can be blocked out so as to suppress effects on a signal detected by the second conductor wiring P2. An upper limit of the thickness d2 of the second laminated material 22 is practically desired to be 1 mm or smaller.

In the flat detector of this exemplary embodiment, the first conductor wiring P1 and the second conductor wiring P2 are disposed in such a manner as to confront each other at a predetermined interval. In addition, in the flat detector of the exemplary embodiment, by the one sides of the first holding material 11 and the second holding material 21 being made to match each other, the interval or space becomes constant which is defined between the first conductor wiring P1 and the second conductor wiring P2 which are disposed to confront each other.

In this flat detector, a medium such as sheet is passed through the first conductor wiring P1 and the second conductor wiring P2. In the event that a magnetic material configuring an object to be detected is applied to this medium, the magnetic poles of the magnetic material are reversed by an alternate field generated from the first conductor wiring P1 (magnetization reversal). The second conductor wiring P2 detects a signal generated by the magnetization reversal occurring in the magnetic material. Consequently, in the event that the signal so generated is detected by the second conductor wiring, it is determined that the medium passing by is the medium to which the magnetic material is applied. On the other hand, in the event that the signal is not detected by the second conductor wiring P2, it is determined that the medium passing by is not the medium to which the magnetic material is applied.

Second Exemplary Embodiment

Figure 2:
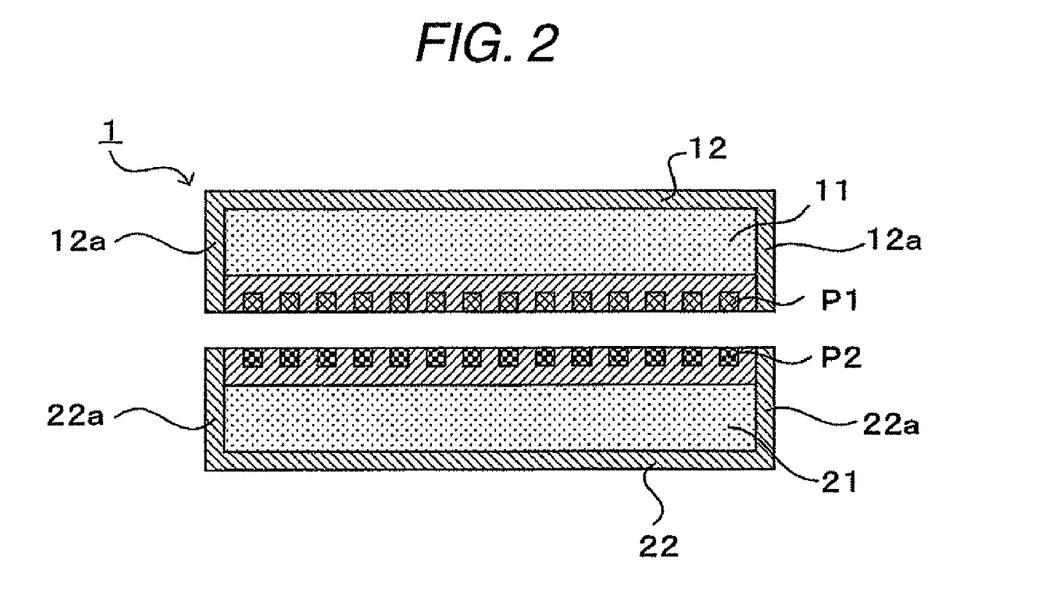
FIG. 2 is an exemplary sectional view illustrating the configuration of a flat detector according to a second exemplary embodiment.

FIG. 2 is an exemplary sectional view illustrating the configuration of a flat detector according to a second exemplary embodiment. The flat detector 1 according to the second exemplary embodiment is different from the flat detector 1 according to the first exemplary embodiment in the configurations of a first laminated material 12 and a second laminated material 22. Since the configurations of other constituent components such as a first conductor wiring P1, a first holding material 11, a second conductor wiring P2 and a second holding material 21 are the same as those of the first exemplary embodiment, hereinafter, different features will mainly be described.

The first laminated material 12 of the flat detector 1 of the second exemplary embodiment is attached to the other side of a first holding material 11. In addition, the first laminated material 12 has portions 12a which are provided to be attached to lateral sides of the first holding material 11 and a first conductor wiring P1, in addition to the portion which is attached to the other side of the first holding material 11. By this configuration, the first laminated material 12 is formed in such a manner as to cover other than an exposed surface of the first conductor wiring P1.

The first laminated material 12 is made of a nonmagnetic metal. For example, aluminum, copper, stainless steel, brass, titanium, or zinc is used. The first laminated material 12 blocks out noise which comes round to enter from the lateral sides of the first conductor wiring P1.

The second laminated material 22 of the flat detector 1 of the second exemplary embodiment is attached to the other side of a second holding material 21. In addition, the second laminated material 22 has portions 22a which are provided to be attached to lateral sides of the second holding material 21 and a second conductor wiring P2, in addition to the portion which is attached to the other side of the second holding material 21. By this configuration, the second laminated material 22 is formed in such a manner as to cover other than an exposed surface of the second conductor wiring P2.

The second laminated material 22 is made of a nonmagnetic metal. For example, aluminum, copper, stainless steel, brass, titanium, or zinc is used. The second laminated material 22 blocks out noise which comes round to enter from the lateral sides of the second conductor wiring P2.

Third Exemplary Embodiment

Figure 3:
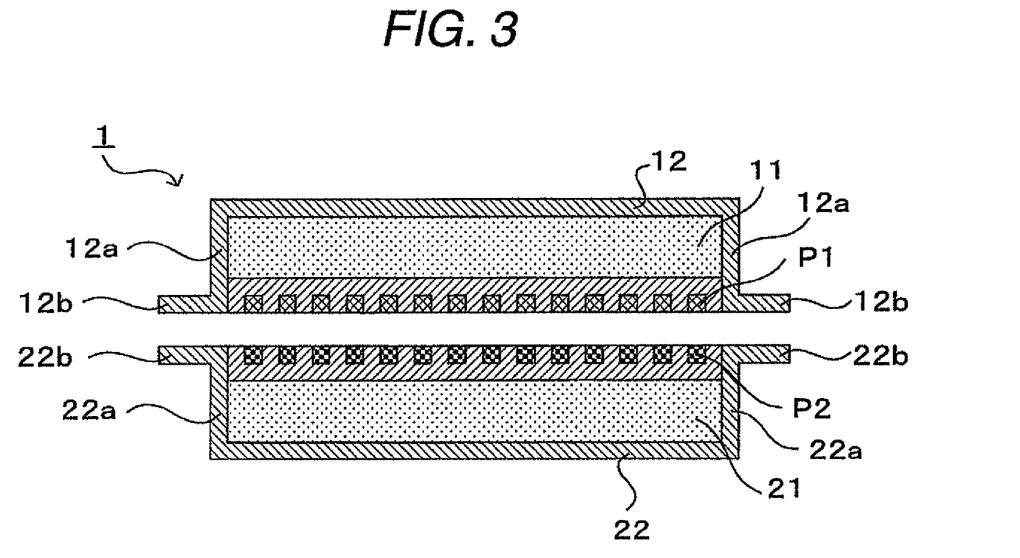
FIG. 3 is an exemplary sectional view illustrating the configuration of a flat detector according to a third exemplary embodiment.

FIG. 3 is an exemplary sectional view illustrating the configuration of a flat detector according to a third exemplary embodiment. The flat detector 1 according to the third exemplary embodiment is different from the flat detector 1 according to the second exemplary embodiment in the configurations of a first laminated material 12 and a second laminated material 22. Since the configurations of other constituent components such as a first conductor wiring P1, a first holding material 11, a second conductor wring P2 and a second holding material 21 are the same as those of the second exemplary embodiment, hereinafter, different features will mainly be described.

The first laminated material 12 of the flat detector 1 according to the third exemplary embodiment is attached to the other side of a first holding material 11. In addition, the first laminated material 12 has portions 12a which are provided to be attached to lateral sides of the first holding material 11 and a first conductor wiring P1, in addition to the portion which is attached to the other side of the first holding material 11. Further, the first laminated material 12 also has portions 12b which are provided to extend from the portions 12a attached to the lateral sides of the first conductor wiring P1 to extensions from a surface thereof.

The first laminated material 12 is made of a nonmagnetic metal. For example, aluminum, copper, stainless steel, brass, titanium, or zinc is used. The first laminated material 12 blocks noise which comes round to enter from the lateral sides of the first conductor wring P1 and noise which comes round to enter from above the extensions from the surface of the first conductor wiring P1. Namely, noise is blocked out which attempts to enter the flat detector 1 from both an upstream side and a downstream side of the transportation path of the medium to which the magnetic material is applied and which configures the object to be detected.

The second laminated material 22 of the flat detector 1 according to the third exemplary embodiment is attached to the other side of a second holding material 21. In addition, the second laminated material 22 has portions 22a which are provided to be attached to lateral sides of the second holding material 21 and a second conductor wiring P2, in addition to the portion which is attached to the other side of the second holding material 21. Further, the second laminated material 22 also has portions 22b which are provided to extend from the portions 22a attached to the lateral sides of the second conductor wiring P2 to extensions from a surface thereof.

The second laminated material 22 is made of a nonmagnetic metal. For example, aluminum, copper, stainless steel, brass, titanium, or zinc is used. The second laminated material 22 blocks noise which comes round to enter from the lateral sides of the second conductor wiring P2 and noise which comes round to enter from above the extensions from the surface of the second conductor wiring P2. Namely, noise is blocked out which attempts to enter the flat detector 1 from both the upstream side and the downstream side of the transportation path of the medium to which the magnetic material is applied and which configures the object to be detected.

Fourth Exemplary Embodiment

Figure 4:
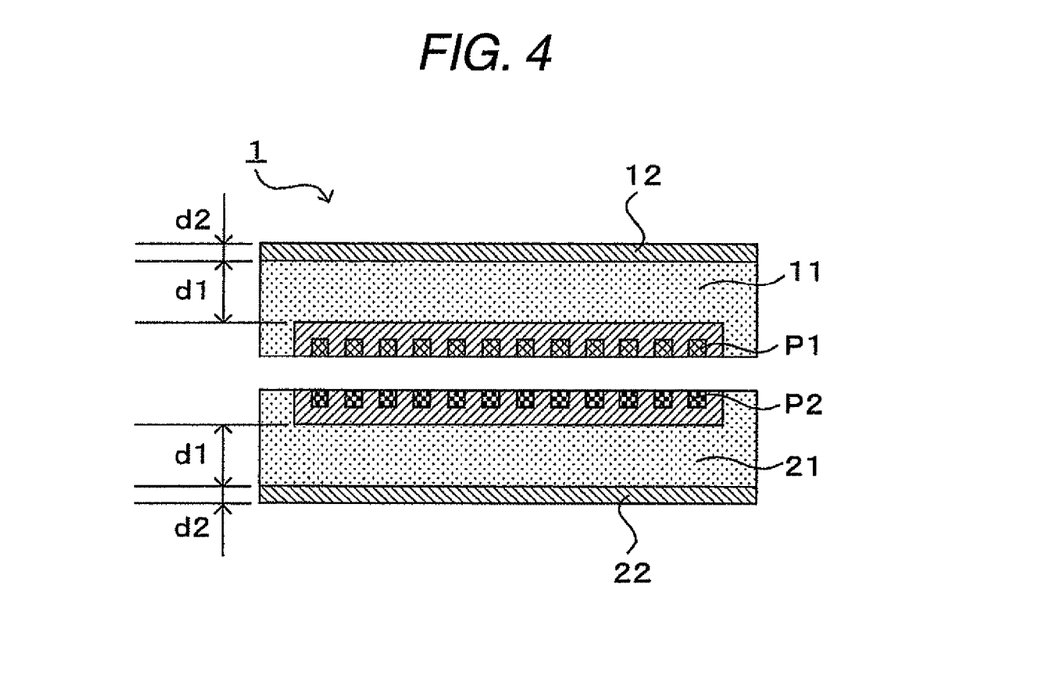
FIG. 4 is an exemplary sectional view illustrating the configuration of a flat detector according to a fourth exemplary embodiment.

FIG. 4 is an exemplary sectional view illustrating the configuration of a flat detector according to a fourth exemplary embodiment. The flat detector 1 according to the fourth exemplary embodiment is different from the flat detector 1 according to the first exemplary embodiment in the configurations of a first holding material 11 and a second holding material 21. Since the configurations of other constituent components such as a first conductor wring P1, a first laminated material 12, a second conductor wiring P2 and a second laminated material 22 are the same as those of the first exemplary embodiment, hereinafter, different features will mainly be described.

The first holding material 11 of the flat detector 1 according to the fourth exemplary embodiment is formed in such a manner as to cover from a back side to lateral sides of the first conductor wiring P1. The first holding material 11 is made of a nonmagnetic nonmetal and suppresses the generation of eddy current better than a case where metal is used therefor. For example, resin, glass or wood is used.

A thickness d1 of the first holding material 11 (a thickness of a portion thereof which extends from a side at a back side of the first conductor wiring P1 to the other side thereof) is made to be a thickness equal to or larger than such a distance that the magnetic field strength of an alternate field generated by the first conductor wiring P1 becomes one gauss or smaller. By the thickness of the first holding material 11 being set to the thickness d1, eddy current flowing to the first laminated material 12 is suppressed. Note that an upper limit of the thickness d1 is practically such that the magnetic field strength of an alternate field to be generated becomes on the order of 0.05 gauss.

A thickness d1 of the first laminated material 12 is 10 µm or larger and 1 mm or smaller. In the event that the thickness d2 is 10 µm or larger, exterior noise is blocked out so as to suppress effects on the alternate field generated by the first conductor wiring P1. An upper limit of the thickness d2 of the first laminated material 12 is practically desired to be 1 mm or smaller.

The second holding material 21 of the flat detector 1 according to the fourth exemplary embodiment is formed in such a manner as to cover from a back side to lateral sides of the second conductor wiring P2. The second holding material 21 is made of a nonmagnetic nonmetal and suppresses the generation of eddy current better than a case where metal is used therefor. For example, resin, glass or wood is used.

A thickness d1 of the second holding material 21 (a thickness of a portion thereof which extends from a side at a back side of the second conductor wiring P2 to the other side thereof is made to be a thickness equal to or larger than such a distance that the magnetic field strength of an alternate field generated by the second conductor wiring P2 becomes one gauss or smaller. By the thickness of the second holding material 21 being set to the thickness d1, eddy current flowing to the second laminated material 22 is suppressed. Note that an upper limit of the thickness d1 is practically such that the magnetic field strength of an alternate field to be generated becomes on the order of 0.05 gauss.

The second laminated material 22 is attached to the other side of the second holding material 21. The second laminated material 22 is made of a nonmagnetic metal. For example, aluminum, copper, stainless steel, brass, titanium or zinc is used. The second laminated material 22 blocks out exterior noise.

Fifth Exemplary Embodiment

Figure 5:
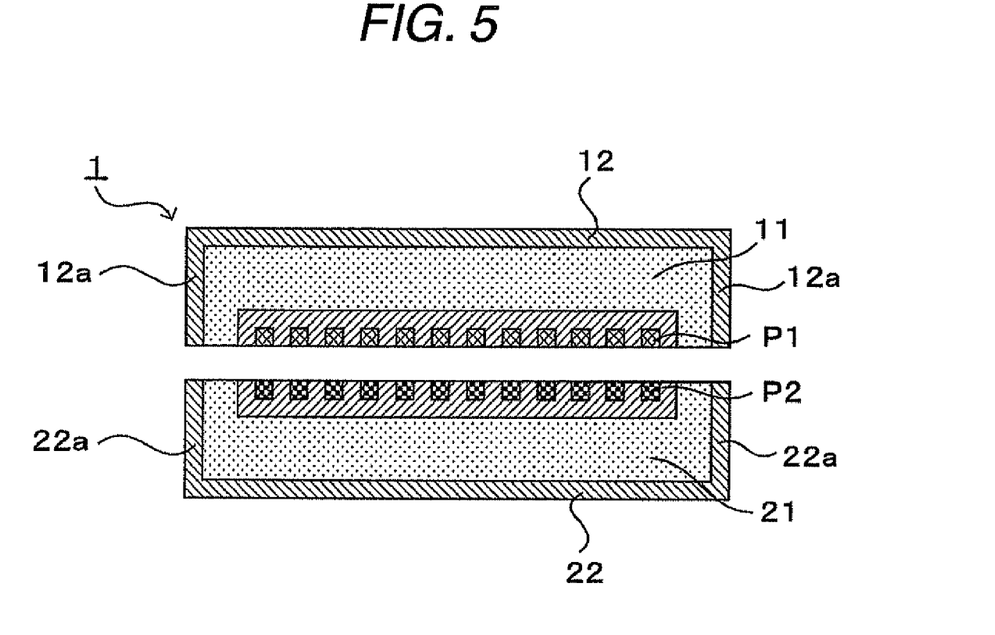
FIG. 5 is an exemplary sectional view illustrating the configuration of a flat detector according to a fifth exemplary embodiment.

FIG. 5 is an exemplary sectional view illustrating the configuration of a flat detector according to a fifth exemplary embodiment. The flat detector 1 according to the fifth exemplary embodiment is different from the flat detector 1 according to the fourth exemplary embodiment in the configurations of a first laminated material 12 and a second laminated material 22. Since the configurations of other constituent components such as a first conductor wiring P1, a first holding material 11, a second conductor wiring P2 and a second holding material 21 are the same as those of the fourth exemplary embodiment, hereinafter, different features will mainly be described.

The first laminated material 12 of the flat detector 1 according to the fifth exemplary embodiment is attached to the other side of the first holding material 11. In addition, the first laminated material 12 includes portions 12a which are provided to be attached to lateral sides of the first holding material 11, in addition to the portion which is attached to the other side thereof.

The first laminated material 12 is made of a nonmagnetic metal. For example, aluminum, copper, stainless steel, brass or zinc is used. This first laminated element 12 blocks out noise which comes round to enter from the lateral sides of the first conductor wiring P1.

The second laminated material 22 of the flat detector 1 according to the fifth exemplary embodiment is attached to the other side of the second holding material 21. In addition, the second laminated material 22 includes portions 22a which are provided to be attached to lateral sides of the second holding material 21, in addition to the portion which is attached to the other side thereof.

The second laminated material 22 is made of a nonmagnetic metal. For example, aluminum, copper, stainless steel, brass or zinc is used. This second laminated element 22 blocks out noise which comes round to enter from the lateral sides of the second conductor wiring P2.

Sixth Exemplary Embodiment

Figure 6:
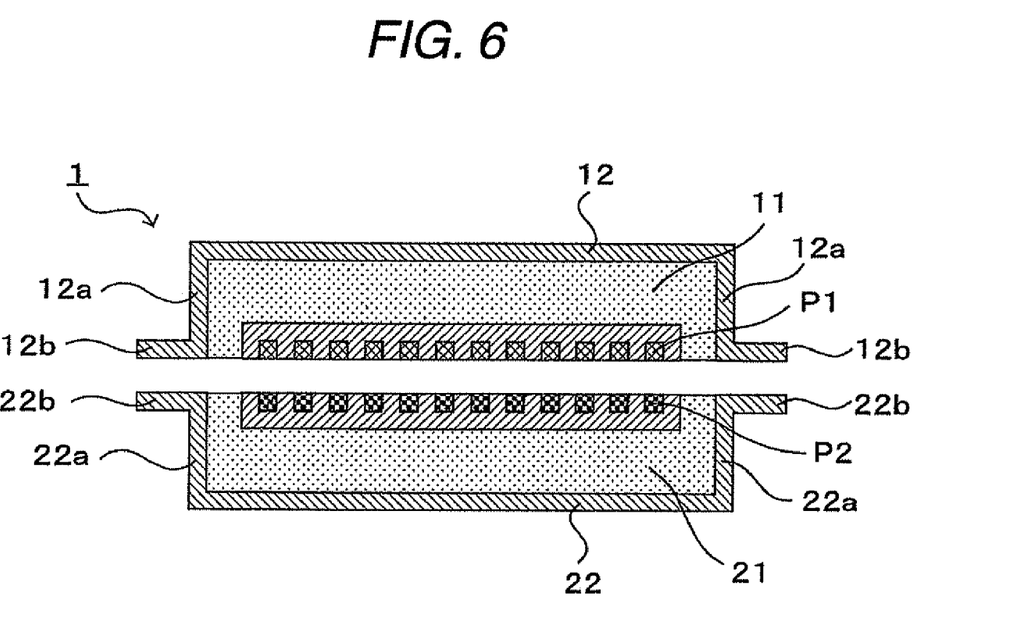
FIG. 6 is an exemplary sectional view illustrating the configuration of a flat detector according to a sixth exemplary embodiment.

FIG. 6 is an exemplary sectional view illustrating the configuration of a flat detector according to a sixth exemplary embodiment. The flat detector 1 according to the sixth exemplary embodiment is different from the flat detector 1 according to the fifth exemplary embodiment in the configurations of a first laminated material 12 and a second laminated material 22. Since the configurations of other constituent components such as a first conductor wiring P1, a first holding material 11, a second conductor wiring P2 and a second holding material 21 are the same as those of the fifth exemplary embodiment, hereinafter, different features will mainly be described.

The first laminated material 12 of the flat detector 1 according to the sixth exemplary embodiment is attached to the other side of the first holding material 11. In addition, the first laminated material 12 includes portions 12a which are provided to be attached to lateral sides of the first holding material 11, in addition to the portion which is attached to the other side thereof. Further, the first laminated material 12 also includes portions 12b which are provided to extend from the portions 12a which are attached to the lateral sides of the first conductor wiring P1 to extensions from a surface thereof.

The first laminated material 12 is made of a nonmagnetic metal. For example, aluminum, copper, stainless steel, brass, titanium, or zinc is used. The first laminated material 12 blocks noise which comes round to enter from the lateral sides of the first conductor wiring P1 and from above the extensions from the surface of the first conductor wiring P1. Namely, noise is blocked out which comes from both an upstream side and a downstream side of the transportation path of the medium to which the magnetic material is applied and which configures the object to be detected.

The second laminated material 22 of the flat detector 1 according to the sixth exemplary embodiment is attached to the other side of the second holding material 11. In addition, the second laminated material 22 includes portions 22a which are provided to be attached to lateral sides of the second holding material 21, in addition to the portion which is attached to the other side thereof. Further, the second laminated material 22 also includes portions 22b which are provided to extend from the portions 22a which are attached to the lateral sides of the second conductor wiring P2 to extensions from a surface thereof.

The second laminated material 22 is made of a nonmagnetic metal. For example, aluminum, copper, stainless steel, brass, titanium, or zinc is used. The second laminated material 22 blocks noise which comes round to enter from the lateral sides of the second conductor wiring P2 and from above the extensions from the surface of the second conductor wiring P2. Namely, noise is blocked out which comes from both an upstream side and a downstream side of the transportation path of the medium to which the magnetic material is applied and which configures the object to be detected.

Other Exemplary Embodiments

Figure 7:
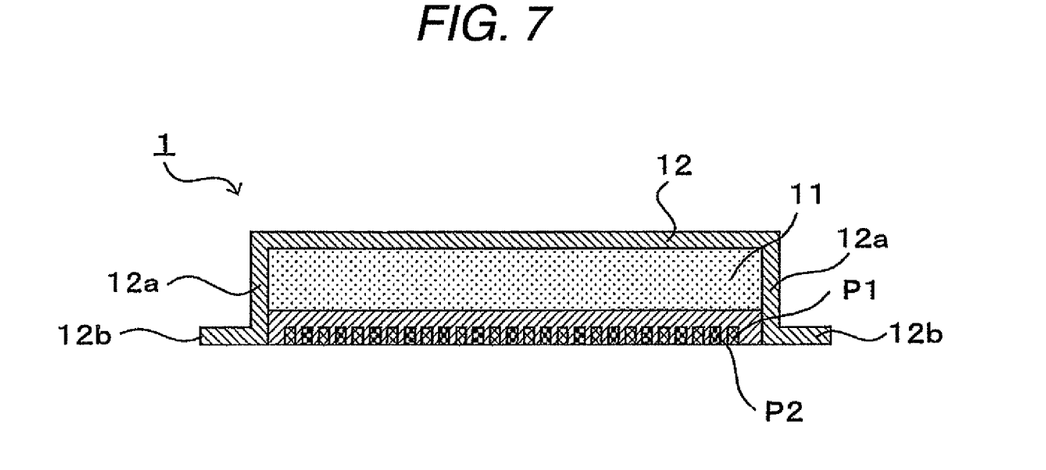
FIG. 7 is an exemplary sectional view illustrating a first one of other exemplary embodiments.
Figure 8:
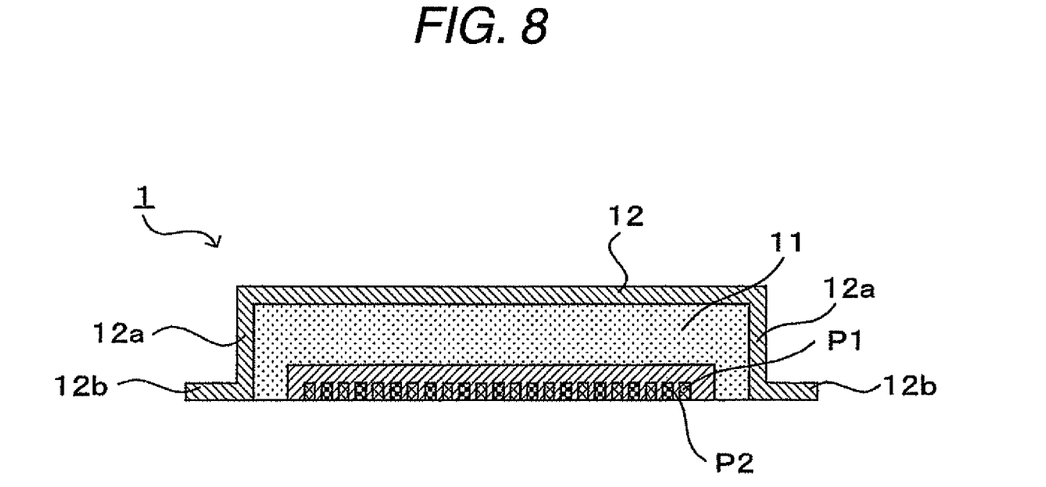
FIG. 8 is an exemplary sectional view illustrating a second one of the other exemplary embodiments.

FIGS. 7, 8 are exemplary sectional views illustrating other exemplary embodiments. These other exemplary embodiments configure examples in which both a first conductor wiring P1 and a second conductor wiring P2 are provided on one side of a first holding material 11. Although a configuration like this can be applied to all the first to sixth exemplary embodiments shown in FIGS. 1 to 6, respectively, here, an example in which the configuration is applied to the configuration of the third exemplary embodiment is shown in FIG. 7, and an example in which the configuration is applied to the configuration of the sixth exemplary embodiment is shown in FIG. 8.

In a flat detector 1 shown in FIG. 7, a first conductor wiring P1 and a second conductor wiring P2 are formed on the same insulation material in such a manner that the first conductor wiring P1 and the second conductor wiring P2 are separated electrically and the insulation material is then attached to one side of a first holding material 11.

In addition, a first laminated material 12 is attached to the other side of the first holding material 11. In addition, the first laminated material 12 includes portions 12a which are provided to be attached to lateral sides of the first holing material 11 and the first conductor wiring P1, in addition to the portion which is attached to the one side of the first holding material 11. Further, the first laminated material 12 also includes portions 12b which are provided to extend from the portions 12a which are attached to the lateral sides of the first conductor wiring P1 to extensions from a surface thereof.

In a flat detector 1 shown in FIG. 8, a first conductor wiring P1 and a second conductor wiring P2 are formed on the same insulation material in such a manner that the first conductor wiring P1 and the second conductor wiring P2 are separated electrically and the insulation material is then attached to one side of a first holding material 11. In addition, the first holding material 11 is formed in such a manner as to cover the first conductor wiring P1 and the second conductor wiring P2 as far as lateral sides thereof.

In addition, a first laminated material 12 is attached to the other side of the first holding material 11. In addition, the first laminated material 12 includes portions 12a which are provided to be attached to lateral sides of the first holing material 11, in addition to the portion which is attached to the one side of the first holding material 11. Further, the first laminated material 12 also includes portions 12b which are provided to extend from the portions 12a which are attached to the lateral sides of the first conductor wiring P1 to extensions from a surface thereof.

In these flat detectors 1, a medium such as sheet is passed by in the vicinity of an exposed surface where the first conductor wiring P1 and the second conductor wiring P2 are provided. In the event that a magnetic material which configures an object to be detected is applied to this medium, the magnetization of the magnetic material is reversed by an alternate field generated from the first conductor wiring P1 (magnetization reversal). The second conductor wiring P2 detects a signal that is generated by the magnetization reversal in the magnetic material. Consequently, in the event that the signal is detected by the second conductor wiring P2, it is determined that the medium passing by is the medium to which the magnetic material is applied. On the other hand, in the event that the signal is not detected by the second conductor wiring P2, it is determined that the medium passing by is not the medium to which the magnetic material is applied.

<2. Medium Detector>

[Configuration of Detector]

Figure 9:
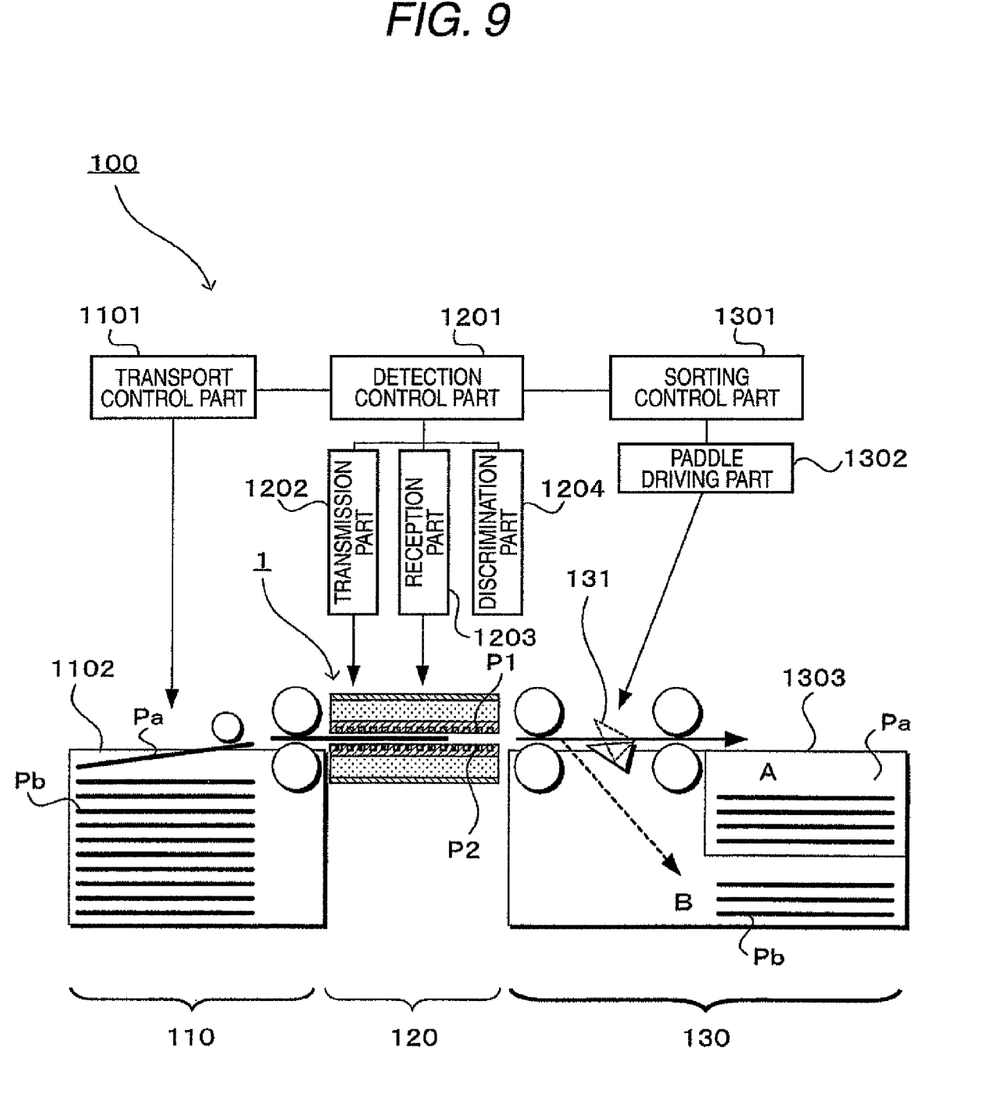
FIG. 9 is a block diagram illustrating a medium detector according to an exemplary embodiment of the invention.

FIG. 9 is a block diagram illustrating a medium detector according to an exemplary embodiment of the invention. A medium detector 100 includes a transport unit 110, a detection unit 120, and a sorting unit 130. The medium detector 100 sorts out media such as sheets which are fed out of the transport unit 110. Specifically the medium detector 100 sorts out media into media to which a magnetic material is applied and media to which no magnetic material is applied. In addition, the medium detector 100 may have a function to sort out media by detecting specific information according to arrangements of magnetic materials that are applied thereto. Although media are mainly sheets, they may take other forms. Here, the description will be made based on the assumption that media to which magnetic materials are applied are referred to as Pa, and media to which magnetic materials are not applied are referred to as Pb.

The transport unit 110 includes a transport control part 1101 and an accommodation part 1102 for accommodating media Pa, Pb therein. The transport control part 1101 gives an instruction to a transport roll at a predetermined timing to feed out media Pa, Pb accommodated in the accommodation part 1102 sheet by sheet towards the detection unit 120.

The detection unit 120 includes the flat detector 1 according to the invention, a detection control part 1201, a transmission part 1202, a reception part 1203 and a discrimination part 1204. The flat detector 1 according to the invention may be any of the flat detectors according to the exemplary embodiments that have been described above. Here, as an example, the flat detector 1 according to the first exemplary embodiment is to be used.

The detection control part 1201 controls the transmission part 1202, the reception part 1203 and the discrimination part 1204. The transmission part 1202 includes an excitation circuit which causes a current to flow to the first conductor wiring P1 of the flat detector 1 so as to generate an alternate field. The reception unit 1203 controls the capture of a signal detected by the second conductor wiring P2 of the flat detector 1. The discrimination part 1204 performs a discriminating operation between a medium Pa and a medium Pb based on the signal captured by the reception part 1203.

The sorting unit 130 includes a sorting control part 1301, a paddle driving part 1302, and a sorting and accommodation part 1303. The sorting control part 1301 receives the result of a discrimination carried out at the discrimination part 1204 of the detection unit 120 and then gives an instruction to the paddle driving part 1302.

The paddle driving part 1302 drives a paddle 131 in response to an instruction sent thereto from the sorting control part 1301, so as to switch orientations of the paddle 131. At least two sorting areas A, B are provided in the sorting and accommodation part 1303. In the sorting unit 130, a medium Pa is sorted into the sorting area A and a medium Pb into the sorting area B by the orientation of the paddle 131.

[Medium Detecting Operation]

Firstly, an instruction is given from the transport control part 1101 to the accommodation part 1102 of the transport unit 110, so as to drive the transport roll in the accommodation part 1102 to thereby feed out media Pa, Pb accommodated in the accommodation part 1102 sheet by sheet to the detection unit 120.

In the detection unit 120, a current is applied to the first conductor wiring P1 from the transmission part 1202 so as to generate an alternate field. The media Pa, Pb so fed out of the accommodation part 1102 of the transport unit 110 ten pass by in the vicinity of the flat detector 1 of the detection unit 120. As this occurs, the magnetization of the magnetic material applied to the medium Pa is reversed by an alternate field generated from the first conductor wiring P1 of the flat detector 1, and a signal is generated from the medium Pa by virtue of the magnetization reversal occurring therein. On the other hand, such a signal is not generated in the medium Pb to which no magnetic material is applied.

The second conductor wiring P2 of the flat detector 1 detects a signal that is generated by the magnetization reversal occurring in the magnetic material during the passage of the media Pa, Pb in the vicinity of the flat detector 1. A signal captured at the reception part 1203 is sent to the discrimination part 1204, where the existence of a signal that has been generated by the magnetization reversal in the magnetic material is determined. The result of determination on the existence of such a signal is sent to the detection control part 1201 by the discrimination part 1204.

The detection control part 1201 sends the determination result sent thereto from the discrimination part 1204 to the sorting control part 1301. Here, the detection control part 1201 sends the determination result to the control part 1301 before distal ends of the media Pa, Pb pass through the detection unit 120 to reach the position where the paddle 131 of the sorting unit 130 resides.

The sorting control part 1301 gives an instruction to the paddle driving part 1302 in accordance with the determination result sent thereto from the detection control part 1201. Namely, when the determination result indicates that the signal has been detected in the media, then, understanding that the medium is the medium Pa to which the magnetic material is applied, the sorting control part 1301 sends to the paddle driving part 1302 an instruction to switch the orientation of the paddle 131 so that the medium Pa is sent to the sorting area A. On the other hand, when the determination result indicates that the signal has not been detected in the medium, then, understanding that the medium is the medium Pb to which no magnetic material is applied, the sorting control part 1301 sends to the paddle driving part 1302 an instruction to switch the orientation of the paddle 131 so that the medium Pb is sent to the sorting area B.

The paddle driving part 1302 switches the orientation of the paddle 131 according to the instruction given thereto by the sorting control part 1301. This switching is to be completed before the distal ends of the media Pa, Pb have arrived at the paddle 131, whereby the medium Pa to which the magnetic material is applied is sent to the sorting area A, while the medium Pb to which no magnetic material is applied is sent to the sorting area B.

In the medium detector 100 according to the exemplary embodiment, transport rollers 1103 for feeding recording media Pa, Pb out of the transport unit 110 into the detection unit 120 and transport rollers 1304 for pulling the recording media Pa, Pb out of the detection unit 120 into the sorting unit 130 are driven by a stepping motor In the event that the flat detector 1 does not have the first holding material 11 and the second holding material 21 which are made of the nonmagnetic nonmetal and the first laminated material 12 and the second laminated material 22 which are made of the nonmagnetic metal, the strength of a signal generated when the second conductor wiring P2 detects noise produced when the stepping motor is switch on/off becomes larger than the strength of a signal generated when the second conductor wiring P2 detects the magnetization reversal in the medium Pa. In this exemplary embodiment, however, by the use of the flat detector 1 described in the first exemplary embodiment, noise produced when the stepping motor is switched on/off is blocked so as to suppress the effects thereof that would otherwise be imposed on the signal detected by the second conductor wiring P2.

APPLICATION EXAMPLE

The medium detector 100 according to the exemplary embodiment may be applied to an image processor of a copier, multifunction equipment, a printer or the like, in addition to the application to a single stand-alone apparatus functioning only to sort out media Pa, Pb.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art The exemplary embodiments were chosen and described in order to best explain the principles of the invention and its practical applications, thereby enabling others skilled in the art to understand the invention for various exemplary embodiments and with the various modifications as are suited to the particular use contemplated. It is intended that the scope of the invention be defined by the following claims and their equivalents.

What is claimed is:

1. A flat detector comprising:
   a first flat member and a second flat member both made of a nonmagnetic nonmetal, the first flat member and the second flat member being disposed to face each other with a space therebetween for transporting a medium, the medium having a shape of sheet;
   a first conductive wiring that generates an alternating magnetic field, the first conductive wiring being disposed on a surface of the first flat member facing toward the second flat member;
   a first layer made of a nonmagnetic metal and disposed at least on a surface of the first flat member opposite to the surface on which the first conductive wiring is disposed;
   a second conductive wiring that detects a signal generated by magnetization reversal of a magnetic material contained in the medium, the magnetization reversal being caused by the alternating magnetic field generated by the first conductive wiring, the second conductive wiring being disposed on a surface of the second flat member facing toward the first flat member; and
   a second layer made of a nonmagnetic metal and disposed at least on a surface of the second flat member opposite to the surface on which the second conductive wiring is disposed, wherein
   a thickness of the first flat member is set so that a strength of the alternating magnetic field at a contact surface of the first flat member and the first layer is 1 gauss or smaller.

2. The flat detector according to claim 1, wherein thicknesses of the first layer and the second layer are not less than 10 μM and not more than 1 mm.

3. The flat detector according to claim 1, wherein the first layer covers the first flat member and the first conductive wiring other than a surface of the first conductive wiring facing the space for transporting the medium, and the second layer covers the second flat member and the second conductive wiring other than a surface of the second conductive wiring facing the space for transporting the medium.

4. The flat detector according to claim 3, wherein the first layer further covers an extension of the surface of the first conductive wiring facing the space for transporting the medium, and the second layer further covers an extension of the surface of the second conductive wiring facing the space for transporting the medium.

5. The flat detector according to claim 1, wherein the first flat member covers the first conductive wiring other than a surface of the first conductive wiring facing the space for transporting the medium, and the second flat member covers the second conductive wiring other than a surface of the second conductive wiring facing the space for transporting the medium.

6. The flat detector according to claim 1, wherein the first layer covers the first flat member and the first conductive wiring other than a surface of the first flat member facing the space for transporting the medium and the surface of the first conductive wiring facing the space for transporting the medium, and the second layer covers the second flat member and the second conductive wiring other than a surface of the second flat member facing the space for transporting the medium and the surface of the second conductive wiring facing the space for transporting the sheet like medium.

7. The flat detector according to claim 6, wherein the first layer further covers an extension of the surfaces of the first flat member and the first conductive wiring facing the space for transporting the medium, and the second layer further covers an extension of the surfaces of the second flat member and the second conductive wiring facing the space for transporting the medium.

8. A medium detector comprising:
   a transport unit that transports a medium in which a magnetic material is contained, the medium having a shape of a sheet;
   a flat detector that detects a signal from the magnetic material contained in the medium; and a sorting unit that switches between transportation paths for the medium that has passed through the flat detector in accordance with a result of detection of the signal by the flat detector, wherein the flat detector comprises:
- a first flat member and a second flat member both made of a nonmagnetic nonmetal, the first flat member and the second flat member being disposed to face each other with a space therebetween for transporting the medium;
- a first conductive wiring that generates an alternating magnetic field, the first conductive wiring being disposed on a surface of the first flat member facing toward the second flat member;
- a first layer made of a nonmagnetic metal and disposed at least on a surface of the first flat member opposite to the surface on which the first conductive wiring is disposed;
- a second conductive wiring that detects a signal generated by magnetization reversal of a magnetic material contained in the medium, the magnetization reversal being caused by the alternating magnetic field generated by the first conductive wiring, the second conductive wiring being disposed on a surface of the second flat member facing toward the first flat member; and
- a second layer made of a nonmagnetic metal and disposed at least on a surface of the second flat member opposite to the surface on which the second conductive wiring is disposed, wherein a thickness of the first flat member is set so that a strength of the alternating magnetic field at a contact surface of the first flat member and the first layer is 1 gauss or smaller.

* * * * *